United States Patent [19]

Avitall

[11] Patent Number: 5,087,243
[45] Date of Patent: Feb. 11, 1992

[54] MYOCARDIAL IONTOPHORESIS

[76] Inventor: Boaz Avitall, 4868 North Ardmore Ave., Milwaukee, Wis. 53217

[21] Appl. No.: 539,611

[22] Filed: Jun. 18, 1990

[51] Int. Cl.$^5$ ............................................. A61N 1/30
[52] U.S. Cl. ..................................... 604/20; 128/784; 128/419 D
[58] Field of Search .......... 128/784, 785, 798, 419 D, 128/419 P; 604/20

[56] References Cited

U.S. PATENT DOCUMENTS

| | | |
|---|---|---|
| 4,146,029 | 3/1979 | Ellinwood, Jr. ............ 128/419 P X |
| 4,711,251 | 12/1987 | Stokes . |
| 4,774,951 | 10/1988 | Osypka . |
| 4,784,161 | 11/1988 | Skalsky et al. . |
| 4,817,608 | 4/1989 | Shapland et al. . |
| 4,819,662 | 4/1989 | Heil, Jr. et al. . |

FOREIGN PATENT DOCUMENTS

| | | | |
|---|---|---|---|
| 0348271 | 12/1989 | European Pat. Off. ............ 128/784 |
| 0619190 | 7/1978 | U.S.S.R. ................................ 604/20 |
| 1017348 | 5/1983 | U.S.S.R. ................................ 604/20 |
| 2175207 | 11/1986 | United Kingdom ................ 604/20 |

Primary Examiner—Lee S. Cohen
Attorney, Agent, or Firm—Haugen & Nikolai

[57] ABSTRACT

An implantable iontophoretic delivery system for use in applying medicinal materials rapidly to specific subcutaneous tissue sites of interest in conjunction with an implanted defibrillator is disclosed which uses a subcutaneously situated pouch for supplying medication in conjunction with a pair of defibrillator electrodes connected to a power source. One of the electrodes is located proximately with respect to the tissue of interest and is designed to dispense the medication of interest utilizing controlled electrical pulses. The pouch is connected with the administering electrode of the electrode system via pumping mechanism.

8 Claims, 3 Drawing Sheets

MYOCARDIAL IONTOPHORESIS

BACKGROUND OF THE INVENTION

I. Field of the Invention

The present invention is directed generally to the iontophoretic transport of ions for therapeutic purposes. More particularly, it involves the use of a direct current stimulus to transport cardioactive drugs such as antiarrhythmia, vasodilators, inotropic drugs to cardiac tissue.

II. Discussion of the Related Art

Implantable defibrillator devices have been under development and use for some time. This device is used for the correction of either ventricular tachycardia (abnormally rapid heart rate) or ventricular fibrillation (an extremely rapid heart beat disorder) by discharging electrical energy into the heart normally between internally placed electrodes. The electrode arrangement may include two large patches which are placed on the epicardial or pericardial surface adjacent the heart tissue. When the implantable defibrillator senses or recognizes ventricular tachycardia or fibrillation the implantable defibrillator discharges, normally with about 30 joules of electrical energy via the two patches. The current utilized for the devices is supplied by a battery powered pulse generator implanted under the skin of the patient.

Ventricular arrhythmias in patients with coronary heart disease and myocardial infarction probably originate from the areas of slow conduction within the previously infarcted myocardium region. Most patients with sustained monomorphic ventricular tachycardia have various degrees of myocardial scar secondary to obstructed coronary arteries.

The efficacy of antiarrhythmic medication is related to concentration of the drug at the arrhythmogenic area. Since most antiarrhythmic drugs require high myocardial tissue concentrates to be effective, high dose intake of such drugs will lead to high plasma concentrations and with it high incidence of toxic side effects.

Iontophoretic transport of ions is a technique in which positive or negative ions are driven into tissue of interest by current applied between two electrodes one of which contains a supply of the material to be transported. Iontophoresis for therapeutic purposes by means of a direct current was introduced in 1908 by Leduc. Since then it has been introduced in several fields such as transdermal delivery of steroids to joints, as well as transdermal delivery of local anesthetics, facilitated transdermal transport of insulin, and the like.

A system which provides for the subcutaneous injection of a drug into an implanted reservoir connected to the heart by a pacer lead is described in U.S. Pat. No. 4,774,951 to Osypka. Other references teach the delivery of drugs to a treatment site through techniques and methods such as porous electrode leads, by dissolving slowly from an immobilized site, or by osmosis through a permeable membrane.

SUMMARY OF THE INVENTION

By means of the present invention, appropriate drugs can be transported at high concentration to the site of interest where time and concentration are of the essence. The delivery system maximizes the concentration of the drug in the site of interest and minimizes the systemic concentration of the medication, thereby reducing side effects.

The system generally consists of a pair of electrodes, including anodic and cathodic electrodes, one of which is designed to dispense the medication of interest, proximately located with respect to the tissue of interest and connected by electrical leads to a subcutaneous independent source of electricity. A subcutaneously situated pouch is provided for containing the drugs of interest. The implanted pouch is designed to be subcutaneously replenished through the skin with a relevant drug from time to time. The pouch is connected with the administering electrode of the electrode system via a pumping mechanism connected by a tube from the storage compartment to the proper patch electrode.

In the illustrated embodiment, the medication is an antiarrhythmic drug which may utilize an existing implantable defibrillator device as a power source or it may be connected to a specially designed power source. The implantable defibrillator unit is embedded over the abdomen under the skin and the antiarrhythmic storage compartment is designed to be replenished subcutaneously by connection inlet. The electrical system installed in connection with the automatic implantable cardioverter defibrillator provides the means by which appropriate antiarrhythmic medication is transported and iontophoretically delivered with maximum concentration to the arrhythmogenic site The pumping mechanism is configured to be powered from the implantable defibrillator power source. The implantable pump would be similar to the implantable pumps used primarily for chemotherapy and insulin drug delivery. These include a bellows-type pump manufactured by Infusid Corporation of Sharon, Mass. which can be subcutaneously refilled with a drug. That pump is fluorocarbon charged and the pressure created by the fluorocarbon vapors provides the power for the pump which operates at about 300 mm of mercury greater than atmospheric pressure.

For antiarrhythmia control, the iontophoretic drug delivery system recognizes the arrhythmia and its programmable computerized control system triggers the pumping mechanism in response to runs of ventricular tachycardia. The pump delivers the antiarrhythmic medicine from the storage compartment to the anodal pole of the patch system which is installed over the arrhythmogenic area. Current pulses to the patch electrode accomplish iontophoretic delivery of the drug.

A small amount, such as one milliamp/$cm^2$ or less, of current can be delivered through the anodal patch in approximately 100 msec pulses synchronized with the ventricular depolarization. The iontophoretic current should be delivered during ventricular refractory periods so as to avoid any ventricular depolarization by the iontophoretic system. The drug delivery into the myocardium may occur in response to runs of ventricular tachycardia in an attempt to chemically interrupt the arrhythmia or at fixed intervals to maintain constant tissue levels of the drug. In addition, the medicine can be delivered with implantable defibrillator discharge which will provide the electromotive force which will transport the drug iontophoretically into the myocardium.

BRIEF DESCRIPTION OF THE DRAWINGS

In the drawings wherein like numerals are utilized to designate like parts throughout the same.

DETAILED DESCRIPTION

The present invention relates to iontophoretic delivery of drugs to internal tissue and is illustrated by the application of such a system to an implantable defibrillator. The electrical system of the implantable defibrillator provides the electrical current by which appropriate antiarrhythmic medication can be transported; but, of course, the application of the invention is not intended in any manner to be restricted to use only in conjunction with an implantable defibrillator. The delivery system maximizes concentration drug in the arrhythmic site an minimizes the overall or systemic concentration of the medication, thereby reducing side effects. Since the implantable defibrillator is capable of recognizing ventricular tachycardia or fibrillation, its computerized control system is utilized to trigger a pumping mechanism in response to runs of ventricular tachycardia or at fixed intervals to maintain high drug concentrations in the tissues. Iontophoretic current is controlled to be delivered during ventricular refractory periods to avoid any ventricular depolarization problems.

The pump then can deliver the arrhythmic medication, or any charged cardioactive medication, from a storage compartment to the anodal pole of the patch system which has previously been placed over the arrhythmogenic area of the heart. An example of such system incorporated into the implantable defibrillator will now be described in greater detail with reference to the accompanying drawings.

Figure 1:
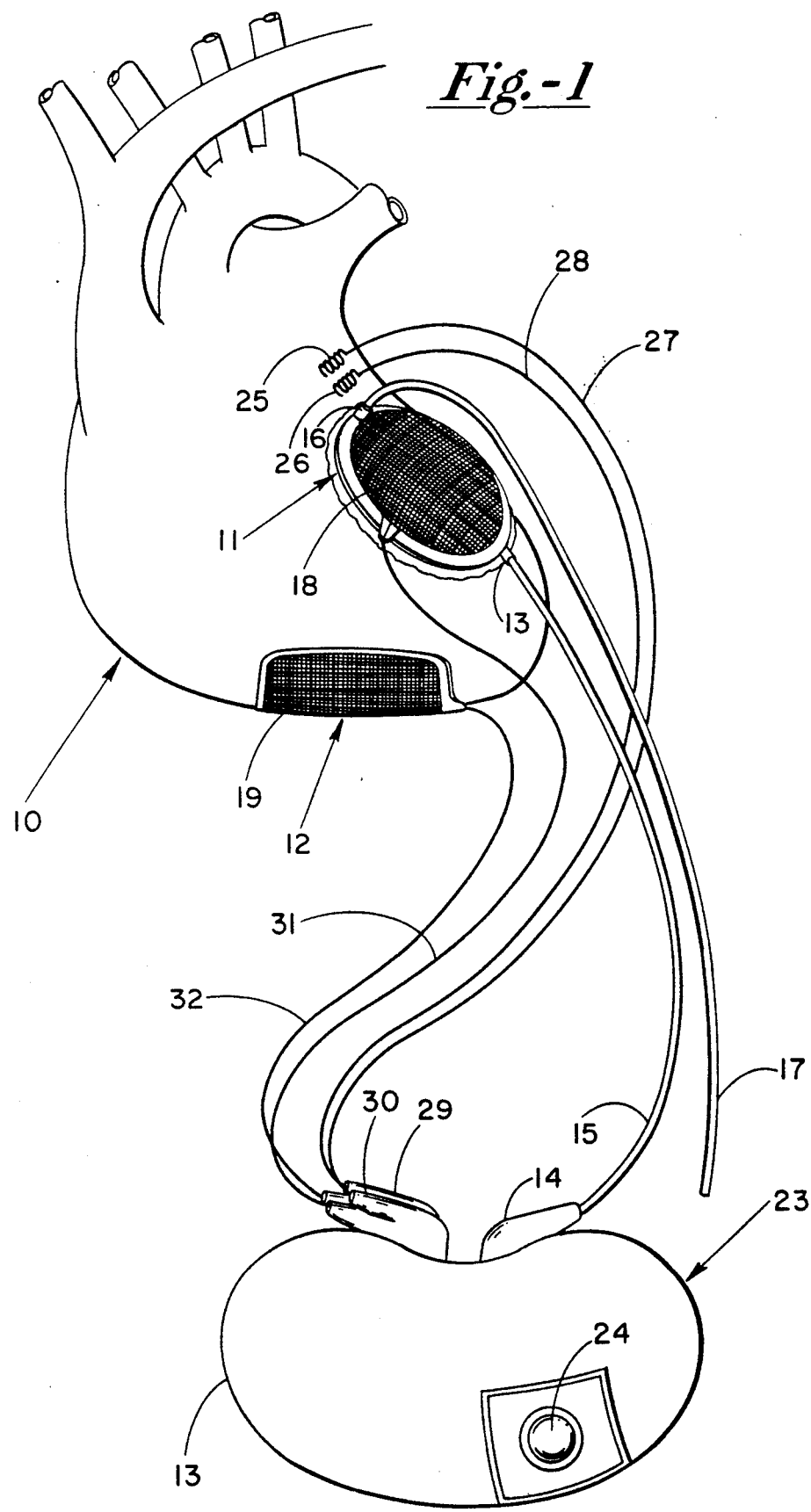
FIG. 1 is a schematic representation of the iontophoresis system of the invention.
Figure 2:
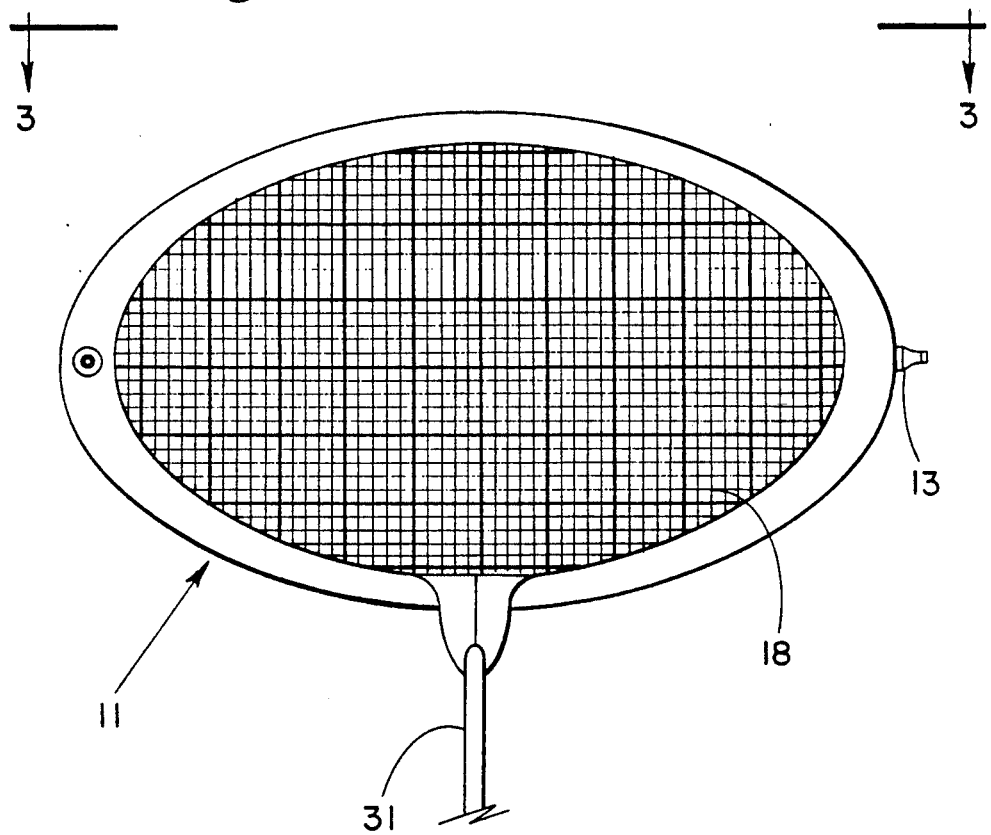
FIG. 2 is a top view of the drug delivering patch electrode in accordance with the invention.
Figure 3:
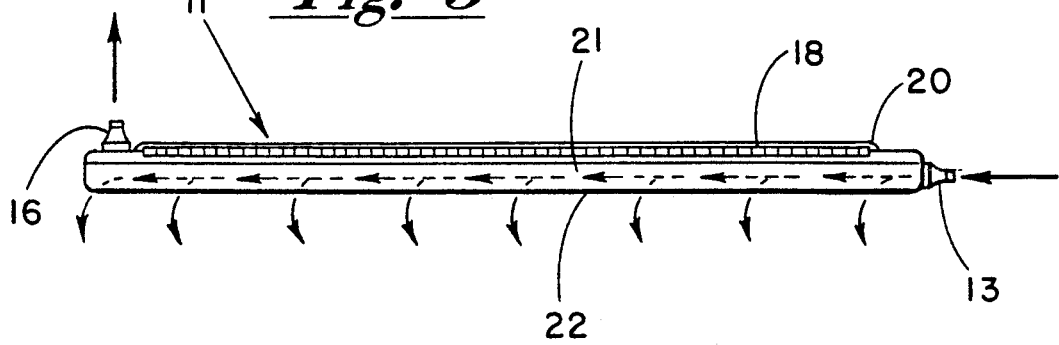
FIG. 3 is a side elevational view of the patch electrode of FIG. 2.

As shown in FIG. 1, the system is installed with reference to the heart of a patient shown generally at 10. It includes a rather large anodal patch electrode 11 which is normally designed to be installed over and addressing a previous infarct or known arrhythmogenic region of the heart. This patch electrode is best depicted in FIGS. 2 and 3. A second patch electrode facing the anterior patch is provided at 12. The anodal electrode 11 has a drug inlet port 13 which is connected to a drug reservoir outlet port 14 via a tube 15 and is also provided with a drug outlet port 16 connected to a discharge tube as at 17.

The electrode 11 also has a conductor grid are 18 in the form of metallic mesh. A similar conductor grid is provided with respect to the cathode 12 as at 19. As can better be seen in FIG. 3, the mesh 18 of the electrode 11 is further covered by an outer silicone lining 20 which overlays the entire system and protects it from the surrounding tissues and body fluids. A similar lining surrounds the system of the electrode 12 similarly protecting it from the surrounding tissues and bodily fluids. The mesh 18 is exposed to the inner chamber 21 of the electrode 11 which, in one embodiment, had a nominal thickness of 4 mm. Chamber 21 interfaces with the epicardial surface to which the patch electrode 11 is attached via permeable membrane 22.

The system is further provided with a chamber 23 which includes a subcutaneous resupply port 24 and contains the batteries or source of electrical current (not shown) for the implantable defibrillator and iontophoresis systems together with the drug pump, also not shown.

Bipolar electrogram electrodes 25 and 26 are attached to the heart via devices 27 and 28 (FIG. 1), respectively, which are attached to input leads 29 and 30 in a well-known manner. These electrodes provide input data with respect to the operation of a heart and act to control the implantable defibrillator and iontophoresis systems in accordance with the invention. Implantable defibrillator electrical leads 31 and 32 are also provided connecting the source of implantable defibrillator electrical energy with the anodic and cathodic patch electrodes, respectively. Since the implantable defibrillator unit is embedded over the abdomen under the skin, the antiarrhythmic storage compartment included in the chamber 23 can be designed to be easily replenished subcutaneously, as via port 24.

Figure 4:
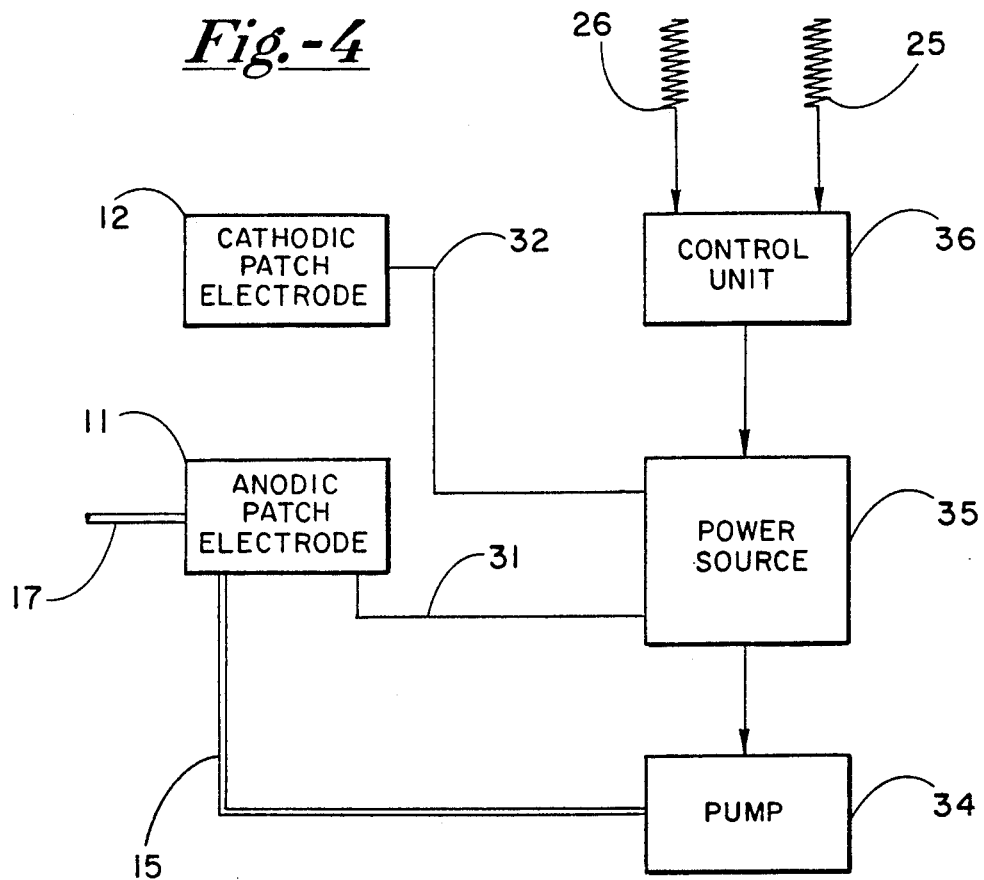
FIG. 4 is a schematic block diagram of the system of the invention.

FIG. 4 is a schematic block diagram of the system of the invention including a pump (34), power source or battery (35), and control device (36) which controls both the power source and pump in relation to inputs from the bipolar electrogram recorded by the sensing electrodes indicating the rhythm state of the heart. As seen in the schematic of FIG. 4, the implantable defibrillator will incorporate the drug chamber and the pump will be powered from the implantable defibrillator power source 35, as determined by the control device 36 which may be microprocessor operated in a well-known manner.

With respect to the pump, currently there are several proven implantable pump systems primarily designed for chemotherapy and insulin drug delivery. One such pump is made by Infusid Corporation of Sharon, Mass. which is fluorocarbon-charge bellows-type pump which can be subcutaneously refilled with a drug. The pressure created by the fluorocarbon vapors provides the power for this pump and it operates at about 300 mm of mercury above atmospheric pressure. In addition, other pumps are under development including peristaltic-type insulin pumps for implant use which ar expected to be available shortly.

Given the state-of-the-art of implantable pumps, incorporation into the iontophoretic drug delivery system within the implantable defibrillator unit is indeed feasible. However, it must be remembered that unlike the long term administration applications for which these pumps have been previously used, the drug delivered in the system of the invention would be transported to the heart tissue quickly a indicated by the condition of the heart or at fixed intervals to maintain constant drug levels within the tissues. Any excess of the drug delivered by the pump to the patch electrode 11 must either be returned to the storage chamber or discarded. It may be secreted into the pericardial or the chest cavity as by tube 17 from which it can be passively absorbed into the systemic circulation of the patient. Even when secreted or vented in this manner, the amount of drug absorbed in the system of the patient will produce systemic concentrations far less than that required to produce any side effects in the patient.

In operation, the implantable defibrillator through the electrodes 25 and 26 recognizes ventricular tachycardia or fibrillation, following this when defibrillation is indicated the implantable defibrillator discharges with approximately 30 joules via the two large patch electrodes 11 and 12 placed on the heart surfaces. In conjunction with this, or in certain instances instead of the delivery of a defibrillating discharge, the system will activate the pump 34 to deliver an amount of drug from the storage area to the anodic or positive patch electrode 11. Simultaneously, a small amount of current such as 1 mA/cm$^2$ adjusted to an amount below the capture threshold is delivered through the anodal patch 5 in approximately 80-100 msec pulses synchronized with the ventricular depolarization. This iontophoretic current is delivered during ventricular refractory so as to avoid any ventricular depolarization by the iontophoretic system. The drug delivery into the myocardium may occur at fixed intervals to sustain constant tissue concentration or in response to runs of ventricular tachycardia as recognized by the electrodes 25 and 26 and in an attempt to chemically interrupt the arrhythmia. It can be delivered with the implantable defibrillator discharge so as to prevent recurrence of tachyrhythmias and the necessity of multiple discharges by the implantable defibrillator.

Preliminary studies performed on dogs have indicated that the delivery of antiarrhythmic drugs such as procainamide can be done quite successfully. Procainamide is a highly charged and small molecule; and, thus, is are especially well suited for iontophoretic delivery.

Animal studies have been performed during the last 18 months. Procainamide drug concentration was evaluated in the coronary sinus as well as in systemic circulation. In addition, drug concentration was evaluated transmyocardially using HPLC techniques in areas of chronically infarcted myocardium and in non-infarcted myocardium, areas which were not exposed to iontophoretic transport. Procainamide concentration in the myocardial tissues was 100 times of what is expected to be delivered using IV route. The concentration was much higher in the epicardial surface than in the endocardial surface. However, even within the endocardial surface, drug concentration was sufficient to render sustained monomorphic ventricular tachycardia noninducible for over three hours. On the other hand, tissues remote from the site of iontophoretic transport had very low concentration of procainamide detected and no electrical changes were noted in them.

Given these preliminary results use of the invention is extremely encouraging with respect to the efficacy of the iontophoretic drug transport. It is believed that a great deal better control of life threatening arrhythmic conditions can be achieved by means of the drug delivery system of the invention.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. An implantable iontophoretic delivery system for use in applying medicinal materials rapidly to specific tissue sites of interest comprising:

a source of electrical current;

pulse generating means associated with the source of electric current for generating a series of electric current pulses;

first and second electrodes adapted to be proximately positioned with respect to the tissue site of interest and connected by leads to the source of electrical current, wherein the first electrode further includes means adapted to receive, contain and dispense medicinal materials from a stored supply thereof into proximate tissue of interest in accordance with a series of benign electric pulses supplied from the pulse generating means and wherein the second electrode is disposed to cooperate with the first electrode to cause infusion of the medicinal material in the desired direction;

storage means for storing a supply of the medicinal materials;

conduit means connecting the storage means with the first electrode;

pump means for supplying an amount of the medicinal materials from the storage means to the first electrode on demand;

circuit means connected to the source for supplying current pulses generated by the pulse generating means to the electrodes;

condition sensing means for sensing medical conditions in the tissue of interest requiring application of the medicinal materials to the tissue of interest; and control means for activating and deactivating the pump means and pulse generating means in response to sensed conditions.

2. The apparatus of claim 1 wherein the tissue of interest is an arrhythmogenic site of infarcted heart tissue, the electrodes are defibrillator patch electrodes and the medicinal material is an antiarrhythmic drug.

3. The apparatus of claim 1 wherein the first electrode further comprises an inlet for receiving medicinal materials connected via the conduit means to the storage means, a storage chamber separated from the tissue by a permeable membrane through which the medicinal material can be infused and a discharge port connected with the storage means through which unused medicinal material can be secreted.

4. An implantable iontophoretic delivery system for use in applying cardiac medications rapidly to specific arrhythmogenic heart tissue sites of interest in conjunction with the operation of an automatic implantable cardioverter/defibrillator (AICD) comprising:

a source of electrical current;

pulse generating means associated with the source of electrical current for generating electric current pulses;

first and second electrodes adapted to be proximately positioned with respect to the tissue site of interest and connected by leads to the source of electrical current for the implantable defibrillator, wherein the first electrode further includes means adapted to receive, contain and dispense cardiac medication from a stored supply thereof into proximate tissue of interest in accordance with a series of benign electric pulses from the pulse generating means and wherein the second electrode is disposed to cooperate with the first electrode in the infusion of medication as desired;

storage means for storing a supply of cardiac medication;

conduit means connecting the storage means with the first electrode;

pump means for supplying an amount of the medication from the storage means to the first electrode on demand;

circuit means connected to the source of electrical current for supplying defibrillating current pulses from the pulse generating means and a series of cardiac medication infusing current pulses from the pulse generating means to the electrodes;

condition sensing means for sensing medical conditions in the tissue of interest requiring defibrillation and/or application of the cardiac medication to the tissue of interest; and control means for activating and deactivating the pump means and both the defibrillation and/or the medicating infusing pulsing in response to sensed conditions or in fixed interval form.

5. The apparatus of claim 4 wherein the electrodes are defibrillator patch electrodes and the cardiac medication is an antiarrhythmic drug.

6. The apparatus of claim 5 wherein the first electrode further comprises an inlet for receiving medication from the storage means via the conduit means, a storage chamber connected to the inlet and separated from the tissue by a permeable membrane through which the cardiac medication can be infused and a discharge port through which unused medication can be secreted.

7. A method of rapidly applying cardiac medication to specific arrhythmogenic heart tissue sites of interest comprising the steps of:

receiving a signal indicative of a cardiac condition requiring the application of the medication;

causing an amount of the mediation to be pumped from an implanted supply thereof to a first electrode of a pair including first and second electrodes proximately positioned with respect to the tissue site of interest and connected to a source of electrical energy; and causing a series of benign electrical current pules to be generated from the source of electrical energy and applied through the electrodes in a manner which produces an infusion of the medication from the first electrode into the tissue.

8. The method of claim 7 wherein the benign electrical current pulses are applied during ventricular refractory periods.

* * * * *